United States Patent [19]

Kremer et al.

[11] Patent Number: 5,097,091
[45] Date of Patent: Mar. 17, 1992

[54] PROCESS FOR THE CATALYTIC GAS PHASE DEHYDROGENATION OF HYDROCARBONS USING TOOTHED-WHEEL SHAPED PARTICLES AS CATALYSTS

[75] Inventors: Hans-Joachim Kremer, Poing, Fed. Rep. of Germany; Jacques M. Dethy, Brussels; Louis Andre, Mons, both of Belgium

[73] Assignee: Süd-Chemie Aktiengesellschaft, Munich, Fed. Rep. of Germany

[21] Appl. No.: 599,666

[22] Filed: Oct. 18, 1990

[30] Foreign Application Priority Data

Oct. 20, 1989 [DE] Fed. Rep. of Germany ....... 3935073

[51] Int. Cl.[5] ............................ C07C 2/64; C07C 5/23; B01J 21/04
[52] U.S. Cl. ................................ 585/444; 585/440; 585/654; 585/661; 502/527; 502/439
[58] Field of Search ............... 585/444, 440, 654, 661; 502/527, 439

[56] References Cited

U.S. PATENT DOCUMENTS

| | | | |
|---|---|---|---|
| 4,328,130 | 5/1982 | Kyan | 252/477 |
| 4,370,261 | 1/1983 | Wunder et al. | 252/460 |
| 4,370,492 | 1/1983 | Wunder et al. | 560/245 |
| 4,402,870 | 9/1983 | Schurmans | 502/439 |
| 4,460,706 | 7/1984 | Imanari et al. | 585/444 |
| 4,549,032 | 10/1985 | Moeller et al. | 585/445 |
| 4,652,687 | 3/1987 | Imai et al. | 585/319 |

FOREIGN PATENT DOCUMENTS

| | | |
|---|---|---|
| 82831 | 6/1983 | European Pat. Off. . |
| 177832 | 4/1986 | European Pat. Off. . |
| 220933 | 5/1987 | European Pat. Off. . |
| 2544185 | 4/1977 | Fed. Rep. of Germany . |
| 3442636 | 6/1979 | Fed. Rep. of Germany . |
| 3521765 | 7/1979 | Fed. Rep. of Germany . |
| 125758 | 5/1977 | German Democratic Rep. . |
| 2193907 | 2/1988 | United Kingdom ................ 502/527 |

OTHER PUBLICATIONS

Chemical Abstract 105:135924m.
Chemical Abstract 92:217816e.
Chemical Abstract 106:67831x.

Primary Examiner—Anthony McFarlane
Assistant Examiner—Nhat Phan
Attorney, Agent, or Firm—Herbert P. Price

[57] ABSTRACT

Toothed-wheel shaped particles are used as catalysts in the dehydrogenation of hydrocarbons, particularly ethylbenzene to styrene.

10 Claims, 6 Drawing Sheets

PROCESS FOR THE CATALYTIC GAS PHASE DEHYDROGENATION OF HYDROCARBONS USING TOOTHED-WHEEL SHAPED PARTICLES AS CATALYSTS

BACKGROUND OF THE INVENTION

The invention pertains to a process for the catalytic gas phase dehydrogenation of hydrocarbons, particularly of alkyl aromatics.

The catalytic gas phase dehydrogenation of hydrocarbons, such as alkyl aromatics, especially of ethylbenzene, but also of saturated or mono-unsaturated aliphatic hydrocarbons such as propane or butene, in the presence of water vapor at an increased temperature (in general in the temperature range of 500° to 700° C.), is a process executed on a large scale industrially. Depending on the type of heat supply, there is an isothermal and an adiabatic form of embodiment of the process. A thorough description of the invention processes for the dehydrogenation of alkyl aromatics is found in "Industrielle Aromatenchemie" ["Industrial Aromatics Chemistry"] by H. G. Frank and J. W. Stadelhofer, Springer Publishing House, Berlin—Heidelberg 1987, pages 142-147. The catalysts used for these processes are metal oxide catalysts. The most effective catalysts contain iron oxide as the primary component, plus oxide-forming alkali metal salts, as well as structure-stabilizing and activity-and selectivity-increasing metal compounds. These types of catalysts are described in EP-A-0 177 832, for example. The catalysts are usually used in the form of molded cylindrical pellets, rarely as tablets, spheres, or rings. The particle diameter of the molded catalysts particles usually varies between 1.5 and 12 mm. For isothermal processes, the particle size must be at least 5 mm on account of the high pressure loss in the tubes of the dehydrogenation reactor. In the radial reactors which are used in adiabatic processes, catalyst pellets with a diameter of approximately 1.5 to 5 mm and a length/diameter ratio of approximately 0.5 to 3 can generally be used in the shorter fixed bed packings.

For kinetic reasons, as small a catalyst particle size as possible is desired, so that maximal yields of the desired dehydrogenion products are obtained from the selective dehydrogenation reaction with only short retention times in the catalyst particle, i.e. for short diffusion distances of the products and products to the activated catalyst surface area and back into the gas phase.

Small particle dimensions cause a high pressure drop, however. For thermodyamic reasons, as low a pressure as possible is desired for the dehydrogenation reaction.

According to DE-AS 25 44 185 and EP-B-0 206,192, which have as their object processes for the catalytic dehydrogenation of alkyl aromatics, particularly of ethylbenzene, this requirement is taken into account by the choice of special catalyst geometries, e.g., cylinder ring, star or cross pellet, and honeycomb shape.

Although an increased catalytic activity relative to cylindrical pellets is attained with the use of this type of molded catalyst particle, the objective remains to further improve the activity and selectivity of the dehydrogenation catalysts via a kinetically more favorable shape, because of the great industrial significance of processes for the catalytic dehydrogenation of hydrocarbons, particularly for the production of styrene.

From DE-A-31 41 942 (U.S. Pat. No. 4,328,130) molded catalyst particles are known with a cylindrical shape with several axial indentations which extend radially from the cylinder periphery inwards and define the elevations lying between them, whose maximum width is larger than that of the indentations. These molded catalyst particles are used for the conversion of hydrocarbons, particularly in the isomerization, alkylation, reforming and hydrogenation, including hydrocracking, hydrotreating, hydrorefining, hydrometallization, hydrodesulfurization, and hydrodenitrification. These reactions are carried out in the liquid phase, and as such, high retention times for liquids are desired, which are promoted by the clover-shaped cross-section in conjunction with the comparably smaller diameter (<0.23 cm) of the molded catalyst particles.

Moreover, said liquid-phase reactions are preferably carried out with carrier catalysts, with aluminum oxide preferably used as the carrier material, onto which metal, metal oxides and metal sulfides from the transition elements (e.g., nickel, cobalt, molybdenum, and/or tungsten) can be applied as the catalytically active substance. These types of catalysts are not suitable for catalytic gas phase dehydrogenation of hydrocarbons, because they are deactivated in a short period of time due to carbon deposits.

SUMMARY OF INVENTION

The invention pertains to a process for the catalytic gas phase dehydrogenation of hydrocarbons, particularly of alkyl aromatics, at elevated temperatures in the presence of water vapor and molded metal oxide catalyst particles. The process is characterized by the fact that for the catalyst, one uses toothed-wheel shaped particles with at least three teeth and the following dimensional ratios:

a. the ratio of crown circle diameter: root circle diameter is approximately 1.2 to 2.5:1;

b. the ratio of gap width on the tooth root: tooth width on the crown is approximately 0.1 to 0.9:1;

c. the gap width on the tooth root is at least 0.1 mm.

The crown circle is the circle made by the crowns or outer surface of the teeth, i.e., the outer circumference of the wheel shaped particle.

The root circle is the circle made by the root or base of the teeth, i.e., the circumference of the inner circle formed at the base of the gap between the teeth.

DESCRIPTION OF THE INVENTION

It has now been found that especially advantageous results are attained in a process for the catalytic gas phase dehydrogenation of hydrocarbons, particularly of alkyl aromatics, at an increased temperature in the presence of water-vapor and molded metal oxide catalyst particles, if one uses toothed-wheel shaped particles with at least three teeth and the following dimensional ratios as the catalysts:

a. the ratio of crown circle diameter: root circle diameter is approximately 1.2 to 2.5:1.

b. the ratio of gap width at the tooth root: tooth width at the crown is 0.1 to 0.9:1.

c. the gap width on the tooth root is at least 0.1 mm.

The terms "crown circle diameter," "root circle diameter," and "tooth height" are taken from the nomenclature of mechanical toothed wheels or sprokets (cf. e.g. Friedrich, *Tabellenbuch Metall- and Maschinentechnik*, 1988, pages 4–45). The crown circle diameter is shown by $d_2$ and the root circle diameter by $d_1$ on FIGS. 1, 4 and 5. The gap width at the tooth root is shown by $b_1$ and the tooth width at the crown by $b_2$ in FIGS. 1, 4 and 5.

The proposed ratio (a) according to the invention between circle diameter ($d_2$) and root circle diameter ($d_1$), which determines the tooth height (h), is important in order to ensure that in a packing and/or ordered arrangement of the molded catalyst particles in the reactor, the crown surface, defined by $b_2$ times the length of the pellet, does not rest on the root circle surface, defined by the gap width on the root circle ($b_1$) times the length of the pellet.

The proposed ratio (b) according to the invention between tooth height (h) and crown circle diameter ($d_2$) is important both to prevent tooth breakage and to reduce the surface contact between the individual molded particles in a reactor packing.

Preferably one uses shaped particles with the following dimensional ratios:

a. the ratio of crown circle diameter ($d_2$): root circle diameter ($d_1$) is approximately 1.3 to 1.6:1, preferably 1.5:1;

b. the ratio of gap width on the tooth root ($b_1$): tooth width on the crown ($b_2$) is approximately 0.2 to 0.6:1;

c. the gap width on the tooth root ($b_1$) is at least 0.15 mm.

In addition, one preferably uses toothed-wheel shaped particles with 5 to 8 teeth each. It has also proven advantageous to use toothed-wheel shaped particles with a crown circle diameter ($d_2$) of at least 0.35 cm, because in this way the pressure drop in the reactor is minimized, particularly if the dehydrogenation reactions are run at a lower pressure. On the other hand, the crown circle diameter ($d_2$) is preferably not more than 1 cm, because the specific areas of larger shaped particles is smaller, which leads to a drop in activity.

One uses toothed-wheel shaped particles with preferably one or more axial canals contained inside the diameter of the root circle ($d_1$).

According to a further preferred embodiment, one uses toothed-wheel shaped particles with essentially parallel tooth flanks on at least one part of the tooth height (h). The risk of breakage can thus be minimized, because a sharp angle is no longer present between tooth crown and tooth flank, such as is the case in, e.g., clover leaf shaped catalysts particles. The strength of the toothed-wheel shaped particles can be further improved by beveling or rounding off the edges on the tooth crown.

Figure 1:
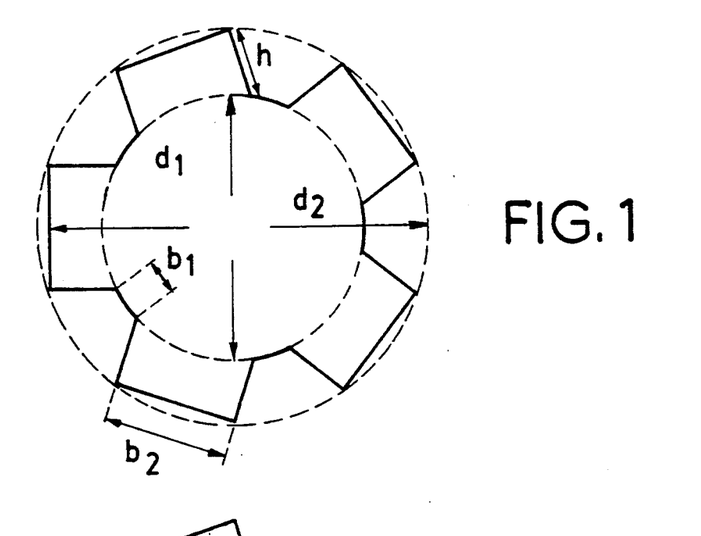
FIG. 1 is a cross-sectional view of a tooth-wheeled cylindrically-shaped catalyst.
Figure 2:
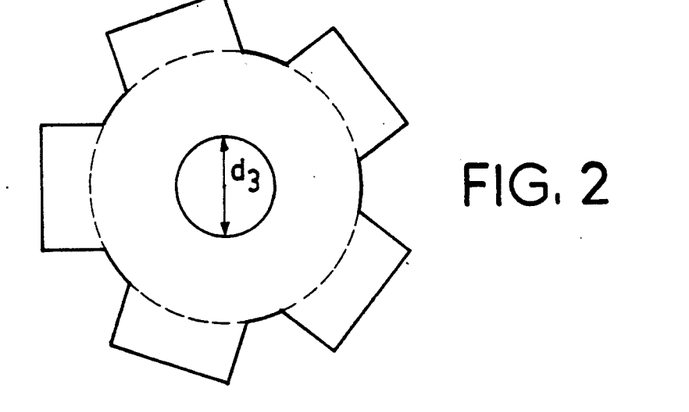
FIG. 2 is a cross-sectional view of a tooth-wheeled cylindrically-shaped catalyst having a smooth circular axial canal in the center of catalyst.
Figure 3:
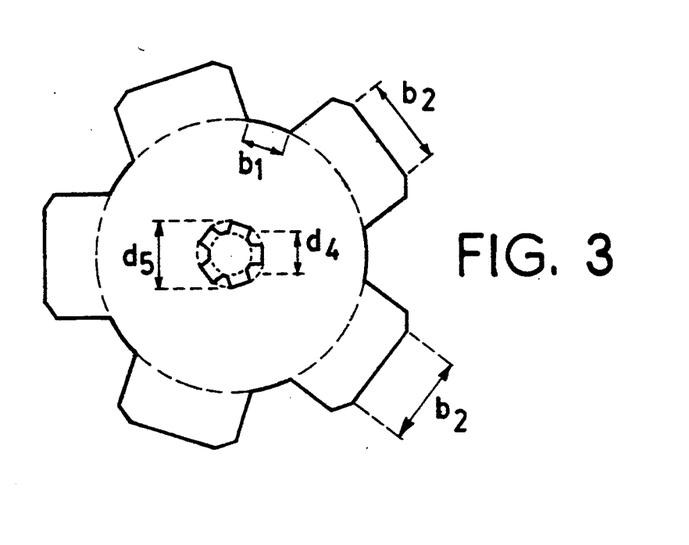
FIG. 3 is a cross-sectional view of a tooth-wheel cylindrically-shaped catalyst having an axial canal in the center of the catalyst which canal has a toothed-wheel shaped cross section.

Several toothed-wheel shaped cross sections of the shaped particles used according to the invention are shown in FIGS. 1 through 3. These are shaped particles with five smoothed-off teeth, the shaped particle of FIG. 1 having no axial canal, while the shaped particle according to FIG. 2 exhibits a smooth axial canal, and the shaped particle according to FIG. 3 exhibits an axial canal with a toothed-wheel shaped cross section.

The individual dimensions are given in FIG. 1. The root circle diameter is indicated with $d_1$, and the crown circle diameter with $d_2$. In FIG. 1, this is identical with the width of the tooth root, but can also be less if the tooth is beveled or rounded off on the edges as is shown in FIG. 3. The width of the tooth gap on the tooth root is indicated with $b_1$. The ratio of the crown circle diameter ($d_2$) to the root circle diameter ($d_1$) is approximately 1.5:1 in the embodiment given; the ratio of the gap width on the tooth root to the tooth width on the crown is approximately 0.27:1.

The length of the shaped particle is generally measured in such a way that the ratio to the crown circle diameter ($d_2$) (which corresponds to the outer diameter of cylindrical pellets) is approximately 0.5 to 5:1, preferably 1 to 3:1. The crown circle diameter is generally approximately 1.5 to 12 mm, preferably 3 to 9 mm. The tooth flanks run essentially parallel over the tooth height (h), as also in the other forms of embodiment, i.e., the tooth flanks standing in a right angle to the tooth crown.

The embodiment according to FIG. 2 shows a smooth, cylindrical axial canal with the diameter $d_3$. In the embodiment in FIG. 3, this axial canal has a toothed-wheel shaped cross section with a crown circle diameter ($d_4$) and a root circle diameter ($d_5$). The other dimensions and/or dimensional ratios correspond to those in FIG. 1.

FIG. 3 shows further that the teeth can be beveled or rounded off on the crown edge, with the tooth width on the crown ($b_2$) larger than the gap width on the tooth root ($b_1$).

In the embodiment of FIG. 3, the beveling and/or rounding off of the edges of the crown has the further advantage that the tooth crowns contact each other on a smaller area in a catalyst packing or an ordered arrangement, so that a larger total free surface area is available. A further advantage of the rounding off and/or beveling of the teeth consists in the fact that abrasion of the catalyst is minimized when it is packed into the reactor and/or when the reactor packing is subjected in the course of operations to vibrations or to stresses caused by temperature and pressure changes, which can lead to a shifting of the pellets relative to each other.

Figure 4:
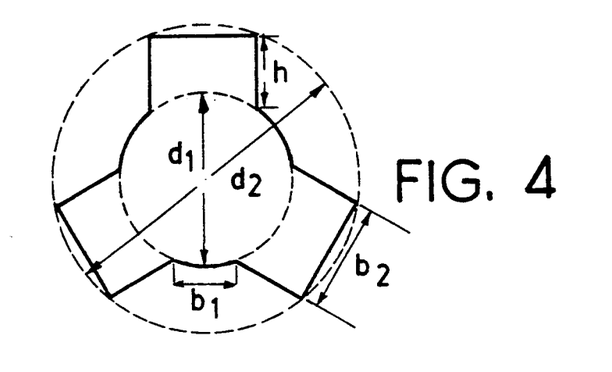
FIGS. 4 and 5 are cross-sectional views of tooth-wheeled cylindrically-shaped catalysts having three teeth and six teeth respectively.
Figure 5:
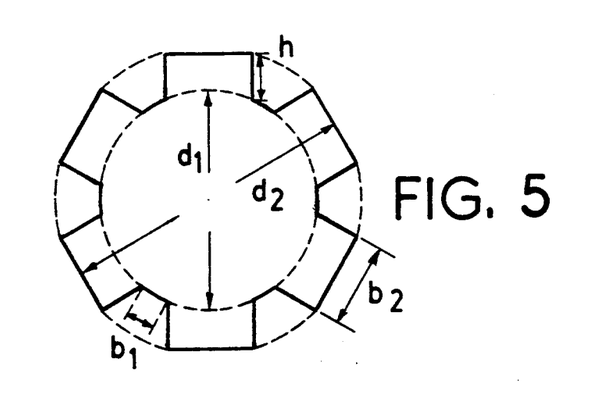

Further embodiments of the molded particle used according to the invention are shown in FIGS. 4 and 5, with FIG. 4 showing a shape with 3 teeth and FIG. 5 a shaped particle with 6 teeth. The individual dimensions are likewise indicated.

The catalysts used in this invention are made with a major amount of iron oxide, i.e., more than 50 weight percent ferric oxide, and minor amounts of other oxides, which can include alkali metal oxides, alkaline earth metal oxides, chromium oxide, oxides of lanthanides, molybdenum oxide, or tungsten oxide. Such catalyst compositions are well known and are described in a number of patents exemplified by U.S. Pat. Nos.

3,904,552; 4,404,123; 4,467,046; 4,628,137; 4,749,674; 4,758,543; and 4,804,799 which are hereby incorporated by reference.

The catalysts can be made by blending the components in the form of oxides, hydroxides, carbonates or decomposable salts with a small amount of water, extruding and molding the blend into the desired shaped particles, drying the shaped particles and calcining them at about 500° C. to about 1000° C. for a time sufficient to form the desired oxides.

The process of this invention is a dehydrogenation process for converting saturated hydrocarbons to olefins and is particularly useful in converting ethylbenzene to styrene. Such dehydrogenation reactions are generally conducted at reaction temperatures from about 500° C. to about 700° C., preferably about 540° C. to about 650° C. The use of subatmopheric, atmospheric, or superatmospheric pressures is suitable. However, based on equilibrium and selectivity considerations, it is preferred to operate at as low a pressure as is feasible. Therefore, atmospheric or subatmospheric pressure is preferred. The dehydrogenation process is conducted as a continuous operation utilizing a fixed bed which may consist of a single stage or a series of stages of the same catalyst in one or several reactors.

In the dehydrogenation process, steam is added to the hydrocarbon feed stock to aid in the removal of carbonaceous residues from the catalyst and to furnish heat for the reaction. Steam to hydrocarbon weight ratios from about 0.6 to about 3 or higher can be used. However, in order to conserve energy in the operation of the process, steam to hydrocarbon weight ratios (S/O) of 2 or lower are preferred.

The contact time of the reactant-containing gas with the catalyst is expressed in terms of liquid-hourly-space velocity (LHSV) which is defined as the volume of liquid hydrocarbon reactant per volume of catalyst per hour. The LHSV of the organic reactants can vary between about 0.3 hr$^{-1}$ and about 5 hr$^{-1}$ and are adjusted within this range to effect the degree of conversion desired for the particular feed in question.

In order to meet kinetic demands on the dehydrogenation catalyst (short diffusion distances in conjunction with low pressure drops), a large geometrical surface area per unit of volume in conjunction with a low pressure drop along the packing of the molded catalyst particles is needed. A measure for this is the activity index (AI), which is calculated from the total area (geometrical surface area) of the molded particle in a liter with the pressure drop $\Delta p$, relative to the molded particle packing in a reactor with a length of 1 m and a diameter of 1 m.

$$AI = \frac{\text{area (cm}^2)}{\text{volume (cm}^3)} \cdot \frac{1}{\Delta p}$$

The pressure drop $\Delta p$ (in Pascals) is calculated from the modified Lewa equation $$p = \frac{2.16 \, H \, G^{1.9}}{b' \, p \, \frac{273}{T} \, D_p}$$

in which H represents the height of the packing (1 m), G represents the cross sectional charge (kg of gas per m$^2$ of free reactor area and sec.), b' represents the density of the gas (kg/m$^3$), p represents the pressure of the gas at the inlet (N/m$^2$), T represents the temperature in K an $D_p$ represents the equivalent diameter of the shape (corresponding to a sphere with the same volume) in m. For the calculation of p in Table I, the following variables were held constant: H, G, b, p, and T, so that $\Delta p$ remains proportional only to $$\frac{1}{D_p^{1.1}}.$$

For the gas, an ethylbenzene - water mixture (weight ratio 1:2.0) was used, with an inlet pressure p of atmospheric pressure and a temperature of 893 K.

Relative to the same external diameter (crown circle diameter) $d_2$, the activity index for molded particles without a central axial canal lies at least 20 percent higher than the smooth cylindrical pellet shapes. For molded particles with a central axial canal, the activity index is increased even further.

In Table I, the pellet dimensions and activity indices for several catalysts shapes used according to the invention are compiled and compared with the known catalyst particles. The values in Table I show that the shapes used according to the invention (examples 3, 6, 10 and 11) have both lower $\Delta p$ values and higher activity indices not only relative to the smooth solid pellet cylinders (examples 1, 2, 4, 5, 9, 12) but also with respect to the star-shaped particles according to DE-AS 25 44 185 (examples 7 and 8).

Figure 6:
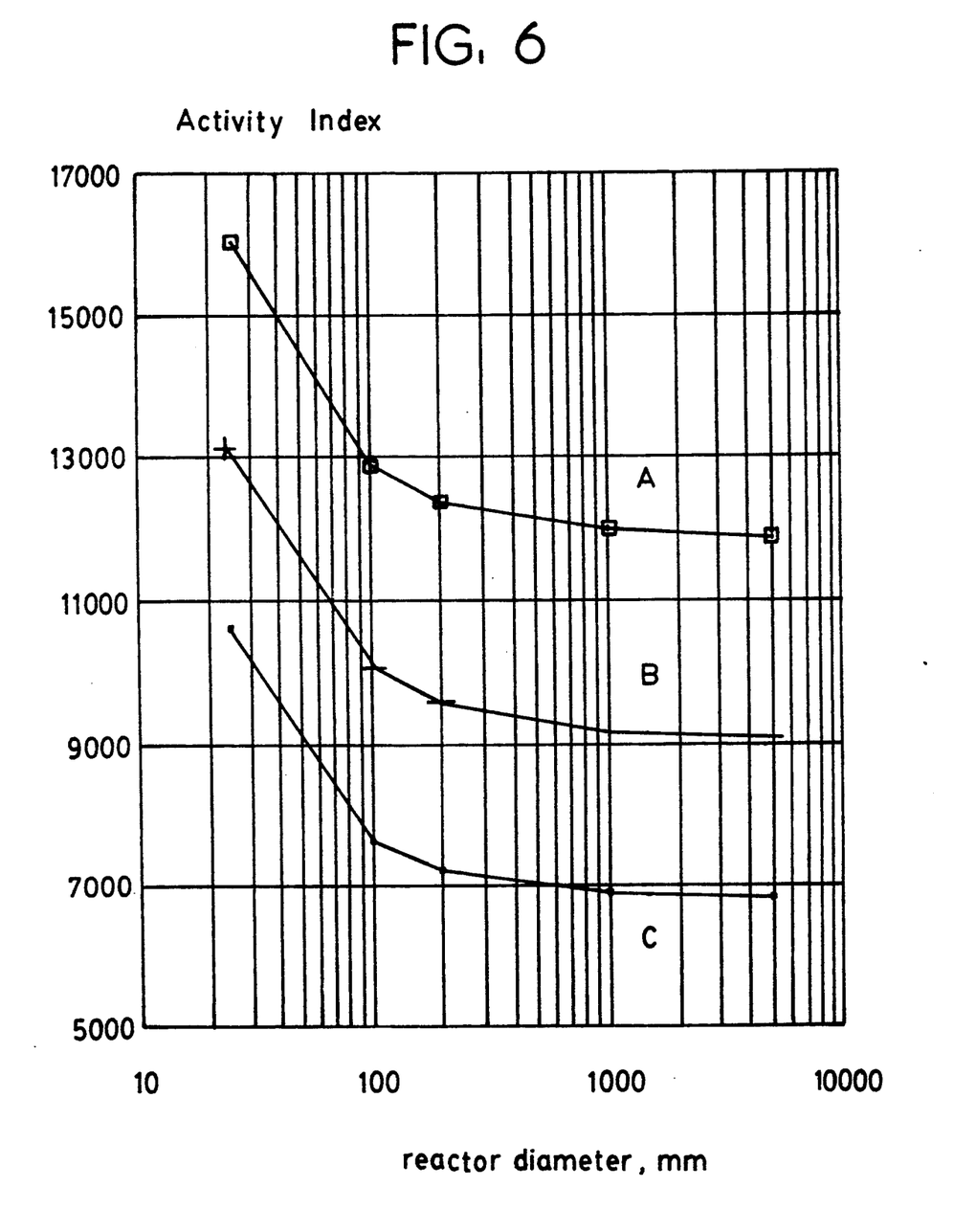
FIG. 6 is a graph of the activity index of catalysts as a function of the reactor diameter.

FIG. 6 gives the activity index as a function of the tube reactor diameter for a shaped particle outer diameter (crown circle diameter $d_2$) of 6 mm and a length of 9 mm. Curve A shows the activity indices of catalysts with a tooth-shaped cross section and central canal corresponding to FIG. 2. Curve B shows the activity indices of shaped particles with toothed-wheel shaped cross section without a central axial canal according to FIG. 1. Curve C shows the activity indices of smooth solid pellet cylinders. The curves clearly show the superiority of the toothed-wheel shapes according to the invention of FIGS. 2 and 1 relative to the smooth solid pellet cylinder. The superiority of the shaped particles used according to the invention is evident not only in isothermal tubular reactors but also in adiabatic fixed bed reactors, with radial or vertical flow.

TABLE I

| Example | outer diameter or crown circle diameter $d_2$ (mm) | length (mm) | axial canal diameter d(mm) | root circle diameter for toothed shapes $d_1$(mm) | ratio $d_2/d_1$ | number of teeth N | $\Delta p$ | AI | Observations |
| --- | --- | --- | --- | --- | --- | --- | --- | --- | --- |
| 1 | 3.0 | 6.0 | — | — | — | 0 | 1.55 | 6380 | reference |
| 2 | 3.5 | 6.0 | — | — | — | 0 | 1.35 | 6460 | " |
| 3 | 3.5 | 6.0 | — | 2.5 | 1.4 | 5 | 1.17 | 8690 | FIG. 1 |
| 4 | 4.0 | 7.0 | — | 4.0 | — | 0 | 1.16 | 6560 | reference |
| 5 | 4.5 | 7.0 | — | — | — | 0 | 1.05 | 6630 | " |
| 6 | 4.5 | 7.0 | — | 3.2 | 1.4 | 5 | 0.90 | 8960 | FIG. 1 |

TABLE I-continued

| Example | outer diameter or crown circle diameter $d_2$ (mm) | length (mm) | axial canal diameter d(mm) | root circle diameter for toothed shapes $d_1$(mm) | ratio $d_2/d_1$ | number of teeth N | $\Delta p$ | AI | Observations |
| --- | --- | --- | --- | --- | --- | --- | --- | --- | --- |
| 7 | 4.5 | 7.0 | — | 2.68 | 1.74 | 6 | 1.25 | 8840 | FIG. 2 from DAS2544185 |
| 8 | 4.5 | 7.0 | — | 2.01 | 2.25 | 4 | 1.21 | 7980 | FIG. 3 from DAS2544185 |
| 9 | 6.0 | 9.0 | — | 0 | — | 0 | 0.77 | 6830 | reference |
| 10 | 6.0 | 9.0 | — | 4.30 | 1.4 | 5 | 0.66 | 9140 | FIG. 1 |
| 11 | 6.0 | 9.0 | 1.75 | 4.30 | 1.4 | 5 | 0.60 | 11990 | FIG. 2 |
| 12 | 9.0 | 13.5 | — | 0 | — | 0 | 0.49 | 7160 | reference |

Figure 7:
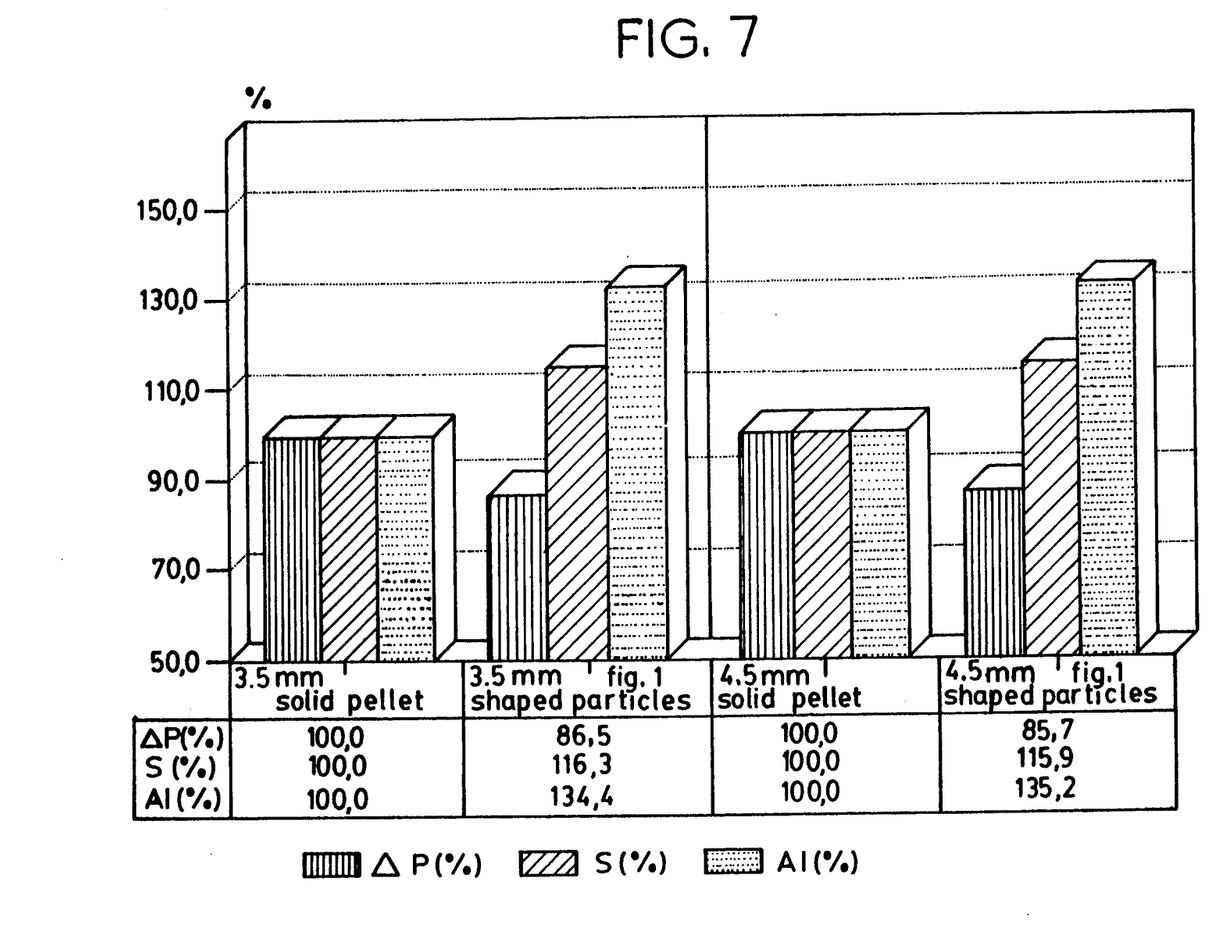
FIGS. 7 and 8 are graphs showing relative activity indices for catalysts.
Figure 8:
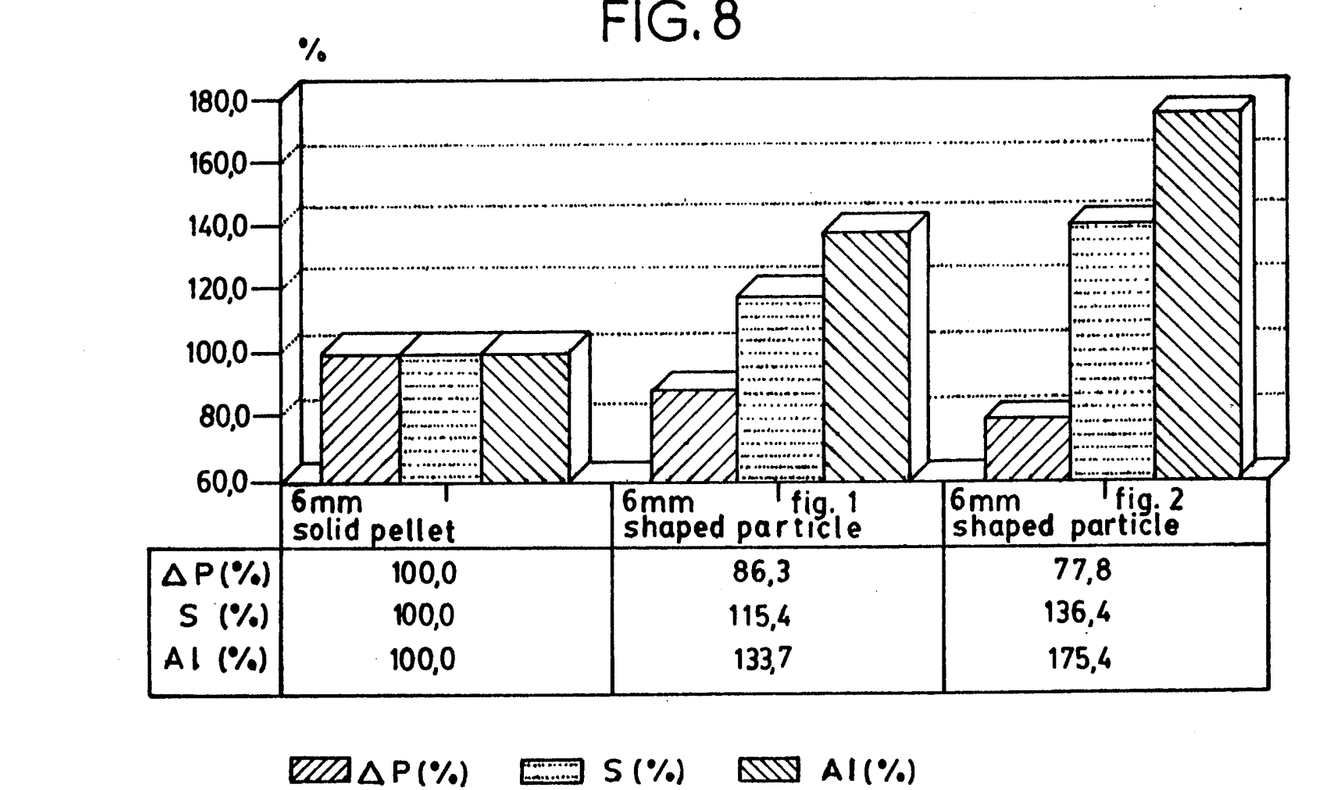

FIGS. 7 and 8 show the relative activity indicers for shaped particle outer diameters (crown circle diameter) of 3.5, 4.5 and 6 mm for the shaped particles used according to the invention, in a direct comparison to cylindrical solid shaped particles. The relative activity index which is given for each in the third column, the relative specific surface areas (first column) and the relative pressure differences (second column) are also given, with the reference shaped particle also set at 100 percent for these parameters.

From this it can be concluded that the shaped particles used according to the invention exhibit higher activity indices at lower $\Delta p$ values and greater surface areas.

The surprising activity and selectivity of the toothed shaped particle is illustrated by means of comparative tests in accordance with the following example of embodiment.

EXAMPLE OF EMBODIMENT

The reference catalysts as well as the catalysts used according to the invention with different outer diameters were produced and tested according to known processes. A process of this type is described, for example, in EP- A 0 177 832, example 7 which is hereby incorporated by reference.

The process consists essentially of taking a mixture of iron (III) oxide, chromium (VI) oxide, potassium carbonate, magnesium carbonate and calcium carbonate, mixing it with water and kneading it. Shaped particles are formed from the extrudable paste obtained, dried, and calcinated for 6 hours at 540° C. The catalyst had the following composition:

| | |
| --- | --- |
| $Fe_2O_3$ | 64.3 percent by weight |
| $Cr_2O_3$ | 3.6 percent by weight |
| $K_2O$ | 24.3 percent by weight |
| MgO | 2.5 percent by weight |
| CaO | 5.3 percent by weight |

Figure 9:
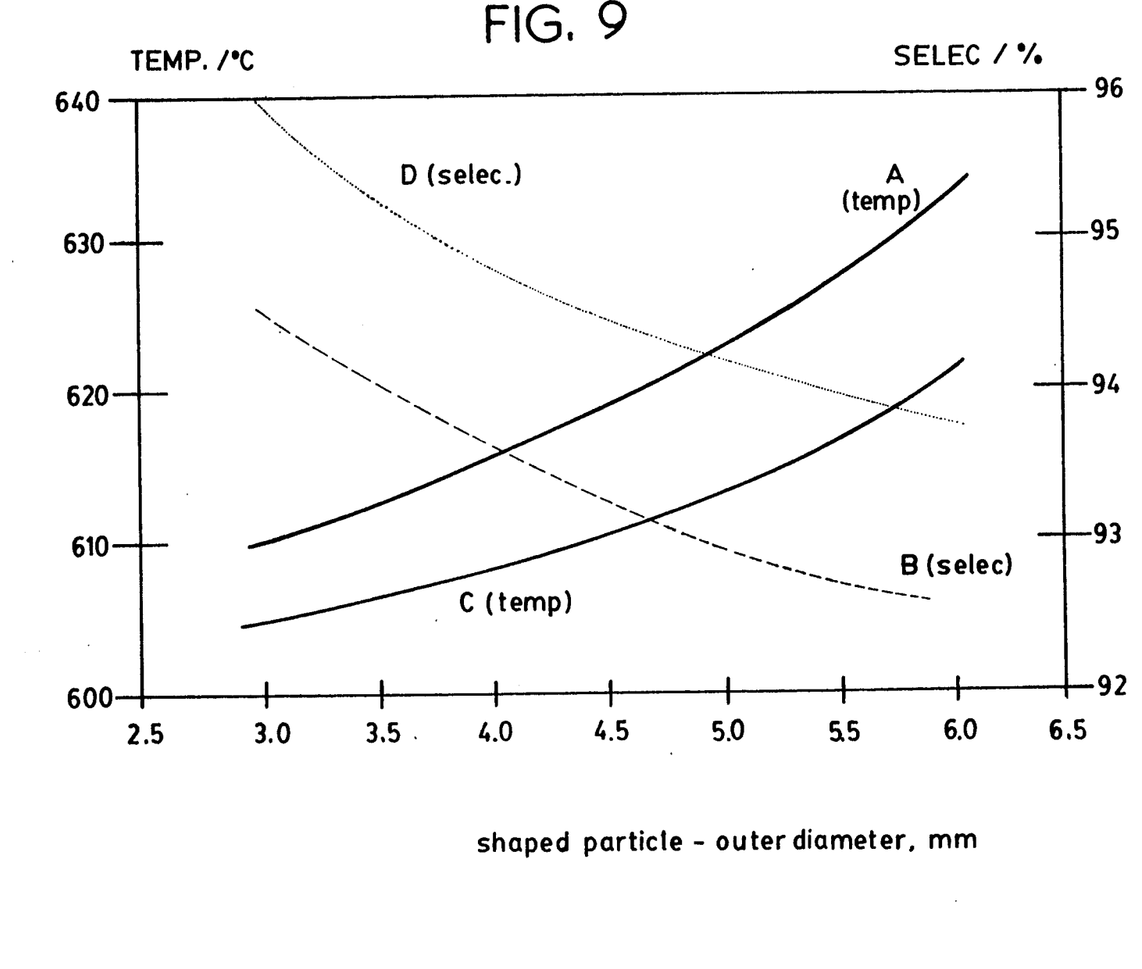
FIG. 9 is a graph of the activity and selectivity of catalysts as a function of outer diameter of the catalyst.

The testing temperature was chosen in such a way that with a steam/ethylbenzene ratio of 2.0 kg/kg, at standard pressure, and with a liquid-hourly-space velocity of 1 liter of ethylbenzene per liter of catalyst per hour, an ethylbenzene conversion of 70 percent by weight was attained. The results are presented graphically in FIG. 9. On the left ordinate, the temperature in °C. is given at which an ethylbenzene conversion of 70 percent by weight was attained. On the right ordinate, the selectivity is given (again at an ethylbenzene conversion of 70 percent by weight) as a percentage based on weight. On the abscissa, the particle diameters (crown circle diameters) are given in mm. Curves A and B show the temperature and selectivity values obtained with the solid pellet cylinders, while curves C and D show the temperature and selectivity values obtained with the toothed shaped particles according to the invention, as a function of the particle diameter. The values given show that a higher activity and selectivity is attainable using the shaped particles according to the invention.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In a process for gas phase catalytic dehydrogenation of hydrocarbons at an elevated temperature in the presence of water vapor, the improvement which comprises using shaped, metal oxide catalyst particles having toothed-wheel shapes with at least three teeth, said teeth having a crown and a root, said crown containing edges, wherein said particles having a crown circle diameter, a root circle diameter, a gap width on the tooth root, and a tooth width on the crown, and wherein said particles having the following dimensional ratios:
   A. a ratio of said crown circle diameter: said root circle diameter being about 1.2 to 2.5:1;
   B. a ratio of said gap width on the tooth root: said tooth width on the crown being about 0.1 to about 0.9:1; and
   C. said gap width on the tooth root being at least 0.1 mm.

2. The process of claim 1 wherein the dimensional ratios are:
   A. the ratio of crown circle diameter: root circle diameter :s about 1.3 to 1.6:1;
   B. the ratio of gap width on the tooth root: tooth width at the crown is about 0.2 to about 0.6:1; and
   C. the gap width at the tooth root is at least 0.15 mm.

3. The process of claim 2 wherein (A) the ratio of crown circle diameter: root circle diameter is 1.5:1.

4. The process of claim 1 wherein the toothed-wheel catalyst particles have 5 to 8 teeth each.

5. The process of claim 1 wherein the crown circle diameter of the catalyst particles is at least about 0.35 cm.

6. The process of claim 1 wherein the toothed-wheel catalyst particles contain one or more axial canals within the root circle diameter.

7. The process of claim 1 wherein at least one portion of each tooth of the toothed-wheel catalyst particles contains flanks parallel to each other.

8. The process of claim 1 wherein the edges on the tooth crowns of the toothed-wheel catalyst particles are beveled.

9. The process of claim 1 wherein the edges on the tooth crowns of the toothed-wheel catalysts particles are rounded.

10. The process of claim 1 wherein ethylbenzene is dehydrogenated to styrene.

* * * * *